US006605586B2

(12) United States Patent
Pisoni

(10) Patent No.: US 6,605,586 B2
(45) Date of Patent: Aug. 12, 2003

(54) PROCESS FOR THE DIRECT PRODUCTION OF SOAP HAVING THE DESIRED CONCENTRATION OF FATTY ACID FROM NEUTRAL FATS

(75) Inventor: Carlo Pisoni, Busto Arsizio (IT)

(73) Assignee: Meccaniche Moderne S.R.L. Chemical Plants Division, Arsizio (IT)

( * ) Notice: Subject to any disclaimer, the term of this patent is extended or adjusted under 35 U.S.C. 154(b) by 3 days.

(21) Appl. No.: 09/773,107

(22) Filed: Jan. 31, 2001

(65) Prior Publication Data

US 2001/0014660 A1 Aug. 16, 2001

(30) Foreign Application Priority Data

Feb. 14, 2000 (EP) .......................................... 00830101

(51) Int. Cl.[7] .............................................. A61K 7/500

(52) U.S. Cl. ...................... 510/458; 510/141; 510/152; 510/153; 510/155; 510/459; 510/481

(58) Field of Search ............................... 510/141, 152, 510/153, 155, 458, 459, 481

(56) References Cited

U.S. PATENT DOCUMENTS

| | | | | |
|---|---|---|---|---|
| 2,159,397 | A | 5/1939 | Mills | 260/415 |
| 2,383,631 | A | 8/1945 | Trent | 260/415 |
| 2,452,724 | A | 11/1948 | Bradshaw | 260/417 |
| 3,657,146 | A | 4/1972 | Fransen | 252/369 |

FOREIGN PATENT DOCUMENTS

| | | |
|---|---|---|
| GB | 379760 | 5/1932 |

*Primary Examiner*—Necholus Ogden
(74) *Attorney, Agent, or Firm*—Abelman, Frayne & Schwab

(57) ABSTRACT

A process for the direct production of soap having the desired concentration of fatty acid from neutral fats by reacting, at a temperature higher than 100° C. and under pressure, an aqueous solution of an alkaline hydroxide or mixture of alkaline hydroxides having a quantity in moles equal to that of the fatty acids contained in the fat and/or oil and a quantity of water equal to that required to obtain the desired concentration of fatty acids in the final soap and heated at a temperature sufficient to obtain a clear solution, with the fat and/or oil previously heated at a temperature at least equal to that of the aqueous solution of the alkaline hydroxide.

9 Claims, No Drawings

PROCESS FOR THE DIRECT PRODUCTION OF SOAP HAVING THE DESIRED CONCENTRATION OF FATTY ACID FROM NEUTRAL FATS

DESCRIPTION

The present invention relates to a process for the production of soap from neutral fats.

More particularly, the present invention relates to a process for the direct production of soap from neutral fats having the required concentration of fatty acids, without the intermediate production of a soap having a lower concentration of fatty acids and the subsequent concentration to reach the requested percentage of said fatty acids.

The process according to the present invention is particularly suitable for the direct production of soaps having a high concentration of fatty acids, for example exceeding 63% by weight.

The term "concentration of fatty acids", as it is used in the present description and claims, is a conventional way to express the concentration of active fat material which represents in a sense the "washing power" of a soap.

As it is known, soaps are alkaline salts of higher fatty acids such as oleic, stearic, palmitic and lauric, etc. acids contained in the form of triglycerides in natural fat substances of vegetable and animal origin. They are obtained by reaction of fats and oils with a strong inorganic base, generally sodium hydroxide sometimes substituted or in mixture with potassium hydroxide.

The result of the reaction between neutral fats or oils and alkaline hydroxide is a mixture of soap, glycerine, (residue of the triglycerides splitting in fatty acids), water and all impurities contained in reagents.

According to the known processes, for the elimination of possible impurities, the thus obtained product is subjected to a washing process which is carried out by dilution with water and subsequent separation of the soap by the addition of an electrolyte (NaCl, another salt or sodium hydroxide), being the soap insoluble in electrolyte solutions over a determined concentration. The majority of water soluble impurities and glycerine are eliminated from the soap by the washing waters.

In common processes for the production of soaps, the sodium hydroxide is fed by an aqueous solution and its concentration is generally lower than about 50%; in fact, aqueous solutions having a higher concentration, at room temperature, show an insoluble bottom material. Moreover, with concentrated hydroxide solutions whose limit depends on the kind of fat or oil used, at atmospheric pressure, the saponification reaction does not start up.

With the known processes, the obtained washed soap has a concentration of fatty acids which is not exceeding 62–63% by weight.

In order to obtain a soap with a higher concentration, such as laundry soap, having a concentration of fatty acids of about 72%, or toilet soap, having a concentration of fatty acids of about 78%–80%, it is necessary to subject the saponification product, after washing, to a concentration process.

The concentration process consists in heating under pressure the hot and liquid soap, coming from the washing phase, at about 80–90° C. and subsequently in spraying the hot under pressure soap in a vacuum chamber. During this operation, the soap loses part of the water, cooling and concentrating at the same time. When coming out of the vacuum concentration plant, the soap, at atmospheric pressure, is in the form of a plastic mass at a temperature of about 30–40° C.

Even though this process is commonly used in industry, it exhibits some drawbacks, which are mainly due to the vacuum itself. In fact, for its processing, the vacuum plant needs a very high vacuum of some mm of Hg, this greatly affects running and ownership costs, moreover it involves operation and maintenance problems.

Another drawback, which is always due to the vacuum concentration process, is the formation of the so-called "dry specks". In fact, during the free expansion of soap, generally going from 2 bars to few mm of Hg, overdried particles of soap called "dry specks" are formed conferring the sandy sensation found in some kinds of soap if a proper treatment to remove said particles is not carried out.

It is an object of the present invention is to avoid the above mentioned drawbacks.

More particularly an, object of the present invention is to provide a saponification process from neutral fats that allows the direct production of a soap, which does not require a further concentration.

A further object of the present invention is to provide a saponification process from neutral fats that allows the direct production of a soap with a concentration of fatty acids having the required concentration of fatty acids, even exceeding 63% and up to 78–80%.

According to the present invention these and other objects which will result from the description, are obtained by a process for the production of soap from neutral fats by reaction of fats and/or oils with an alkaline hydroxide or a mixture of alkaline hydroxides, said process comprises the steps of:

a) preparing an aqueous solution of the alkaline hydroxide or a mixture of alkaline hydroxides having a quantity of hydroxide in moles which is substantially equal to one of the fatty acids contained in the fat and/or oil, and a quantity of water equal to the one necessary to obtain the required concentration of the fatty acids in the final soap;

b) heating the thus obtained aqueous solution at a sufficient temperature to obtain a clear solution of the alkaline hydroxide;

c) heating the fat and/or oil at a temperature at least equal to the one of the alkaline hydroxide aqueous solution;

d) mixing the hot and liquid fat and/or oil with the hot aqueous solution of the alkaline hydroxide in a pressure reactor, and e) completing the reaction at a temperature exceeding 100° C. and under pressure.

The reaction mass thus obtained which is heated and under pressure is then cooled in the form of blocks, noodles or bars.

The aqueous solution of the alkaline hydroxide or mixture of alkaline hydroxides is preferably heated at a temperature exceeding 50° C. and more preferably at a temperature between 90 and 150° C., depending on the hydroxide concentration. Therefore, for example, an aqueous solution containing about 0.305 kmoles of NaOH and about 5.95 kg of water is clear at 110° C., and a solution containing about 0.312 kmoles of NaOH and about 3.55 kg of water is clear at 150° C.

The saponification reaction is preferably carried out at a temperature between 110 and 160° C. and at pressure between 2 and 4 bars.

In order to increase the soap fluidity, sodium chloride or an electrolyte can be added to the alkaline hydroxide aqueous solution; the concentration of sodium chloride or electrolyte can vary between 0.1 and 0.5% by weight with respect to the soap. As stated above, the aqueous solution added to the saponification reactor contains a number of moles of alkaline hydroxide or a mixture of alkaline hydroxides which is substantially equal to one of the fatty acids contained in the fat and/or oil to be saponified and a quantity of water equal to the one needed to obtain the required concentration of fatty acids in the final soap.

Therefore, for instance, in order to obtain a soap having a total amount of fatty acids of about 78% by weight, from a mixture of neutral fats consisting of 80% by weight of tallow and 20% by weight of coconut oil, according to the process of the present invention 65.49 kg of tallow;

16.37 kg of coconut oil;

an aqueous solution of a sodium hydroxide consisting of 12.19 kg of NaOH at 100% (=0.305 kmoles) and 5.95 kg of water heated at 110° C. are used.

The mixture of neutral fats is heated at 120° C. and saponification is carried out at 120–140° C. under pressure.

The thus obtained soap is constituted by:

84.70 kg of anhydrous soap;

9.34 kg of glycerine;

5.96 kg of water

Any fat and natural oil of vegetable and/or animal origin can be used in the process of the present invention. If necessary, fats and oils can be previously subjected to a bleaching and deodorization process according to the required pureness of the final soap.

The process can be batch way or continuously carried out.

The heated product which is under pressure issuing from the saponification reaction is subjected to cooling in continuous or batch way processes in order to obtain soap in the form of blocks, noodles or bars. Any device and/or process, which are well known to this purpose, can be used.

From the above description, the advantages obtained by the process of the present invention are evident. They consist in obtaining the soap with the required concentration of fatty acids directly from the saponification reaction, thus avoiding further washing and concentration processes with all the related problems concerning plant, maintenance, cost and "dry specks" in the final product.

Moreover, the process of the present invention allows the obtaining of a soap with a high concentration of fatty acids, such as 78–80% that could not be directly obtained with the known saponification processes known at the present time.

What is claimed is:

1. A process for the production of soap from neutral fats by reaction of fats and/or oils with an alkaline hydroxide or mixture of alkaline hydroxides, in the absence of a vacuum concentration spraying step, which comprises the steps of:

(a) preparing an aqueous solution of the alkaline hydroxide or the mixture of alkaline hydroxides having a quantity in moles equal to one of the fatty acids contained in the fat and/or oil and a quantity of water equal to the one required to obtain the required concentration of fatty acids in the final soap;

(b) heating the thus obtained aqueous solution at a temperature exceeding 50° C. and to 150° C. to obtain a clear solution of the alkaline hydroxide;

(c) heating the fat and/or oil at a temperature at least equal to one of the alkaline hydroxide aqueous solution;

(d) mixing the hot and liquid fat and/or oil with the hot aqueous solution of the alkaline hydroxide in a pressure reaction; and (e) completing the reaction under pressure at a temperature exceeding 100° C.

2. The process for the production of soap according to claim 1, wherein the product from step e) is cooled in the shape of blocks, noodles or bars.

3. The process for the production of soap according to claim 1, wherein the saponification reaction is carried out at a temperature between 110 and 160° C. and at a pressure between 2 and 4 bar.

4. The process for the production of soap according to claim 1, wherein the solution of the alkaline hydroxide or mixture of alkaline hydroxides contains from 0.1 to 0.5% by weight with respect to soap of NaCl or of an electrolyte.

5. The process for the production of soap according to claim 2, wherein the saponification reaction is carried out at a temperature between 110 and 160° C. and at a pressure between 2 and 4 bar.

6. The process for the production of soap according to claim 3, wherein the saponification reaction is carried out at a temperature between 110 and 160° C. and at a pressure between 2 and 4 bar.

7. The process for production of soap according to claim 2, wherein the solution of the alkaline hydroxide or mixture of alkaline hydroxides contains from 0.1 to 0.5% by weight with respect to soap of NaCl or of an electrolyte.

8. The process for the production of soap according to claim 3, wherein the solution of the alkaline hydroxide or mixture of alkaline hydroxides contains from 0.1 to 0.5% by weight with respect to soap of NaCl or of an electrolyte.

9. The process for the production of soap according to claim 4, wherein the solution of the alkaline hydroxide or mixture of alkaline hydroxides contains from 0.1 to 0.5% by weight with respect to soap of NaCl or of an electrolyte.

* * * * *